US007287318B2

(12) United States Patent
Bhullar et al.

(10) Patent No.: US 7,287,318 B2
(45) Date of Patent: *Oct. 30, 2007

(54) BIOSENSOR

(75) Inventors: Raghbir S. Bhullar, Indianapolis, IN (US); Christopher D. Wilsey, Carmel, IN (US); Brian S. Hill, Avon, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 859 days.

This patent is subject to a terminal disclaimer.

(21) Appl. No.: 10/703,408

(22) Filed: Nov. 7, 2003

(65) Prior Publication Data

US 2004/0163953 A1    Aug. 26, 2004

(51) Int. Cl.
   *H01R 43/00* (2006.01)
(52) U.S. Cl. .................. 29/825; 29/592.1; 29/595; 204/403.01; 204/403.14
(58) Field of Classification Search ............ 29/592.1, 29/595, 825; 204/403.01, 403.14
See application file for complete search history.

(56) References Cited

U.S. PATENT DOCUMENTS

| 4,081,653 A | 3/1978 | Koo et al. ............... 219/121 |
| 4,131,484 A | 12/1978 | Caruso et al. .............. 134/1 |
| 4,233,029 A | 11/1980 | Columbus ................. 23/230 |
| 4,271,119 A | 6/1981 | Columbus ................. 422/50 |
| 4,302,313 A | 11/1981 | Columbus ............... 204/195 R |
| 4,414,059 A | 11/1983 | Blum et al. ............ 156/659.1 |
| 4,477,575 A | 10/1984 | Vogel et al. ............. 436/170 |
| 4,654,127 A | 3/1987 | Baker et al. .............. 205/792 |
| 4,655,880 A | 4/1987 | Liu ....................... 204/403 |
| 4,684,437 A | 8/1987 | Donelon et al. ........... 156/643 |
| 4,849,340 A | 7/1989 | Oberhardt ................. 435/13 |
| 4,865,873 A | 9/1989 | Cole et al. ............... 427/53.1 |
| 4,874,500 A | 10/1989 | Madou et al. ............. 204/412 |
| 4,897,173 A | 1/1990 | Nankai et al. ............ 204/403 |
| 4,963,814 A | 10/1990 | Parks et al. .............. 323/274 |
| 4,975,175 A | 12/1990 | Karube et al. ............ 204/403 |
| 4,999,582 A | 3/1991 | Parks et al. .............. 324/438 |
| 4,999,632 A | 3/1991 | Parks et al. .............. 341/167 |
| 5,018,164 A | 5/1991 | Brewer et al. ............ 372/109 |

(Continued)

FOREIGN PATENT DOCUMENTS

DE    19710358    9/1998

(Continued)

OTHER PUBLICATIONS

Tender, L. et al., Electrochemical Patterning of Self-Assembled Monolayers onto Microscopic Arrays of Gold Electrodes Fabricated by Laser Ablation, *Langmuir*, 1996, 12, 5515-5518.

(Continued)

*Primary Examiner*—Carl J. Arbes
(74) *Attorney, Agent, or Firm*—Jill L. Woodburn; Justin Sage

(57) ABSTRACT

A biosensor is provided that comprises a plate element with a pre-determined reaction zone and a recess positioned adjacent to the reaction zone. The biosensor also comprises a reagent that is positioned on the reaction zone. In preferred embodiments, the recess circumscribes at least a portion of the reaction zone.

29 Claims, 8 Drawing Sheets

U.S. PATENT DOCUMENTS

| | | | |
|---|---|---|---|
| 5,089,103 A | 2/1992 | Swedberg | 204/182.8 |
| 5,104,480 A | 4/1992 | Wojnarowski et al. | 156/643 |
| 5,120,420 A | 6/1992 | Nankai et al. | 204/403 |
| 5,126,034 A * | 6/1992 | Carter et al. | 204/403.05 |
| 5,185,256 A * | 2/1993 | Nankai et al. | 435/174 |
| 5,243,516 A | 9/1993 | White | 435/287 |
| 5,264,103 A | 11/1993 | Yoshioka et al. | 204/403 |
| 5,266,179 A | 11/1993 | Nankai et al. | 204/401 |
| 5,288,636 A | 2/1994 | Pollmann et al. | 435/288 |
| 5,320,732 A | 6/1994 | Nankai et al. | 204/403 |
| 5,334,279 A | 8/1994 | Gregoire | 156/630 |
| 5,336,388 A | 8/1994 | Leader et al. | 204/406 |
| 5,352,351 A | 10/1994 | White et al. | 204/461 |
| 5,366,609 A | 11/1994 | White et al. | 204/403 |
| 5,382,346 A | 1/1995 | Uenoyama et al. | 204/403 |
| 5,385,846 A | 1/1995 | Kuhn et al. | 205/777 |
| 5,390,412 A | 2/1995 | Gregoire | 29/848 |
| 5,391,250 A | 2/1995 | Cheney, II et al. | 156/268 |
| 5,393,401 A | 2/1995 | Knoll | 204/418 |
| 5,395,504 A | 3/1995 | Saurer et al. | 204/403 |
| 5,405,511 A | 4/1995 | White et al. | 205/777 |
| 5,413,690 A | 5/1995 | Kost et al. | 204/403 |
| 5,414,224 A | 5/1995 | Adasko et al. | 174/262 |
| 5,426,850 A | 6/1995 | Fukutomi et al. | 29/848 |
| 5,437,999 A | 8/1995 | Diebold et al. | 435/288 |
| 5,438,271 A | 8/1995 | White et al. | 324/444 |
| 5,451,722 A | 9/1995 | Gregoire | 174/261 |
| 5,465,480 A | 11/1995 | Karl et al. | 29/825 |
| 5,496,453 A | 3/1996 | Uenoyama et al. | 205/777.5 |
| 5,508,171 A | 4/1996 | Walling et al. | 205/777.5 |
| 5,509,410 A | 4/1996 | Hill et al. | 128/637 |
| 5,512,159 A | 4/1996 | Yoshioka et al. | 204/403 |
| 5,512,489 A | 4/1996 | Girault et al. | 205/777.5 |
| 5,520,244 A | 5/1996 | Mundlinger et al. | 165/104 |
| 5,521,060 A | 5/1996 | Hoenes et al. | 435/4 |
| 5,575,930 A | 11/1996 | Tietje-Girault et al. | 216/65 |
| 5,576,073 A | 11/1996 | Kickelhain | 427/555 |
| 5,582,697 A * | 12/1996 | Ikeda et al. | 205/777.5 |
| 5,589,326 A | 12/1996 | Deng et al. | 435/4 |
| 5,593,739 A | 1/1997 | Kickelhain | 427/555 |
| 5,628,890 A | 5/1997 | Carter et al. | 204/403 |
| 5,635,054 A | 6/1997 | Girault et al. | 205/775 |
| 5,682,884 A | 11/1997 | Hill et al. | 128/637 |
| 5,708,247 A | 1/1998 | McAleer et al. | 204/403 |
| 5,739,039 A | 4/1998 | Girault et al. | 436/149 |
| 5,755,953 A | 5/1998 | Henning et al. | 205/778 |
| 5,758,398 A | 6/1998 | Rijnbeek et al. | 29/25.42 |
| 5,759,364 A | 6/1998 | Charlton et al. | 204/403 |
| 5,762,770 A | 6/1998 | Pritchard et al. | 204/403 |
| 5,767,480 A | 6/1998 | Anglin et al. | 219/121 |
| 5,773,319 A | 6/1998 | Chu et al. | 438/39 |
| 5,798,031 A | 8/1998 | Charlton et al. | 204/403 |
| 5,842,787 A | 12/1998 | Koph-Sill et al. | 366/340 |
| 5,846,392 A | 12/1998 | Knoll | 204/403 |
| 5,849,208 A | 12/1998 | Hayes et al. | 216/94 |
| 5,948,289 A | 9/1999 | Noda et al. | 219/121.69 |
| 5,955,179 A | 9/1999 | Kickelhain et al. | 428/210 |
| 5,956,572 A | 9/1999 | Kidoguchi et al. | 438/96 |
| 5,965,001 A | 10/1999 | Chow et al. | 204/600 |
| 5,980,709 A | 11/1999 | Hodges et al. | 204/409 |
| 5,997,817 A | 12/1999 | Crismore et al. | 422/58 |
| 6,004,441 A | 12/1999 | Fujiwara et al. | 204/412 |
| 6,019,944 A | 2/2000 | Buechler | 422/58 |
| 6,103,033 A | 8/2000 | Say et al. | 156/73.1 |
| 6,134,461 A | 10/2000 | Say et al. | 600/345 |
| 6,165,594 A | 12/2000 | Moh et al. | 428/207 |
| 6,175,752 B1 | 1/2001 | Say et al. | 600/345 |
| 6,203,952 B1 | 3/2001 | O'Brien et al. | 430/17 |
| 6,258,229 B1 | 7/2001 | Winarta et al. | 205/403 |
| 6,287,451 B1 | 9/2001 | Winarta et al. | 205/777.5 |
| 6,299,757 B1 | 10/2001 | Feldman et al. | 205/775 |
| 6,309,526 B1 | 10/2001 | Fujiwara et al. | 204/403 |
| 6,338,790 B1 | 1/2002 | Feldman et al. | 205/777.5 |
| 6,399,258 B2 | 6/2002 | O'Brien et al. | 430/17 |
| 6,451,372 B2 * | 9/2002 | Hasegawa et al. | 427/2.13 |
| 6,461,496 B1 * | 10/2002 | Feldman et al. | 205/777.5 |
| 6,592,745 B1 * | 7/2003 | Feldman et al. | 205/777.5 |
| 6,618,934 B1 * | 9/2003 | Feldman et al. | 29/830 |
| 6,645,359 B1 * | 11/2003 | Bhullar et al. | 204/403.01 |
| 6,662,439 B1 | 12/2003 | Bhullar | 29/825 |
| 6,696,008 B2 | 2/2004 | Bradinger | 264/400 |
| 6,776,888 B2 * | 8/2004 | Yamamoto et al. | 204/403.09 |
| 6,966,977 B2 * | 11/2005 | Hasegawa et al. | 204/403.07 |
| 2001/0006766 A1 | 7/2001 | O'Brien et al. | |
| 2003/0088166 A1 | 5/2003 | Say et al. | |
| 2003/0132110 A1 * | 7/2003 | Hasegawa et al. | 204/403.02 |

FOREIGN PATENT DOCUMENTS

| | | |
|---|---|---|
| EP | 0 480 703 A2 | 4/1992 |
| EP | 0 480 703 A3 | 4/1992 |
| EP | 0 593 096 | 4/1994 |
| EP | 0 480 703 B1 | 3/1997 |
| EP | 0 875 754 | 11/1998 |
| EP | 1 098 000 | 5/2001 |
| EP | 1 152 239 A1 | 7/2001 |
| EP | 1 195 441 A1 | 4/2002 |
| EP | 1 202 060 A1 | 5/2002 |
| EP | 1 203 956 A2 | 5/2002 |
| EP | 1 203 956 A3 | 5/2002 |
| EP | 1 288 654 A1 | 3/2003 |
| JP | 56100451 | 8/1981 |
| JP | 01134242 | 5/1989 |
| JP | 01216250 | 11/1989 |
| JP | 2-1535 | 2/1990 |
| JP | 2-128153 | 5/1990 |
| JP | 5-31 5703 | 11/1993 |
| JP | 7-66499 | 3/1995 |
| JP | 7-290751 | 11/1995 |
| JP | 9159644 | 6/1997 |
| JP | 9-260697 | 10/1997 |
| JP | 10-52780 | 2/1998 |
| JP | 10-241992 | 9/1998 |
| JP | 10-275959 | 10/1998 |
| JP | 10-303444 | 11/1998 |
| JP | 11297890 | 10/1999 |
| JP | 2000 097899 | 4/2000 |
| JP | 2000-121594 | 4/2000 |
| JP | 2001-305095 | 10/2001 |
| WO | WO 91/02391 | 2/1991 |
| WO | WO 91/08474 | 6/1991 |
| WO | WO 95/22881 | 8/1995 |
| WO | WO 98/35225 | 8/1998 |
| WO | WO 98/49773 | 12/1998 |
| WO | WO 98/55856 | 12/1998 |
| WO | WO 99/13101 | 3/1999 |
| WO | WO 99/30152 | 6/1999 |
| WO | WO 99/45387 | 9/1999 |
| WO | WO 00/42472 A1 | 7/2000 |
| WO | WO 00/73778 | 12/2000 |
| WO | WO 00/73785 | 12/2000 |
| WO | WI 01/25775 | 4/2001 |
| WO | WO 01/36953 | 5/2001 |
| WO | WO 01/75438 | 10/2001 |
| WO | WO 01/92884 | 12/2001 |
| WO | WO 02/27074 | 4/2002 |
| WO | WO 02/086483 | 10/2002 |

OTHER PUBLICATIONS

Tahhan, Isam, "Biocompatible Microstructuring of Polymers and Electrodes with an Excimer Laser", MEDICS Workshop 2000 Speakers Abstracts, 2 pp.

Sheppard, Jr. et al. "Electrical Conductivity Measurements Using Microfabricated Interdigitated Electrodes", *Anal. Chem.*, 1993, 65, 1199-1202.

Srinivasan R., et al. "Ultraviolet Laser Ablation of Organic Polymers", *Chem. Rev.*, 1989, 89, 1303-1316.

Zongyi, Q., et al. "Excimer Laser Patterning on Thin Polymer Surfaces for Electrochemical Gas Sensors", Polymer Physics Laboratory, Changchun Institute of Applied Chemistry, Chinese Academy of Sciences, Changchun, Peop. Rep. China., Proceedings of the International Conference on Lasers (1999) 21$^{st}$ (Abstract) 1pp.

Tahhan, Isam, "Biocompatible Microstructuring of Polymers and Electrodes with an Excimer Laser", MEDICS Workshop 2000 Speakers Abstracts, 2 pp.

Vaucher et al. "Laser Direct Imaging and Structuring: An Update", http://www.circuitree.com/CDA/ArticleInformation/features/BNP_Features_Item/0.2133.81173.00.html; posted on: Aug. 1, 2002.

Wu, J. et al. "Single-shot Excimer Laser Ablation of Thick Polymer Resists on Metallic Substrates", AMP Journal of Technology vol. 1 Nov. 1991, 69-79.

Srinivasan, R., "Ablation of Polymers and Biological Tisssue by Ultraviolet Lasers", Science, vol. 234, Oct. 21, 1986, 559-594.

Colon, W., "Microanalysis: Biosensors at the Point of Care", MST News 01/04, pp. 9-11.

Duley, W.W. "UV Lasers: effects and applications in materials science", Chapter 3 Photochemical and photothermal effects, Cambridge University Press, pp. 78-97.

LPKF MicrolineLaser II, LPKF Laser & Electronics AG; LPKF; Art.-Nr. 107645-2 (01/00) (2pp.).

Microline Solutions, LPKF Laser & Electronics AG; LPKF; Art.-Nr. 107658-1 (01/00) (3pp.).

\* cited by examiner

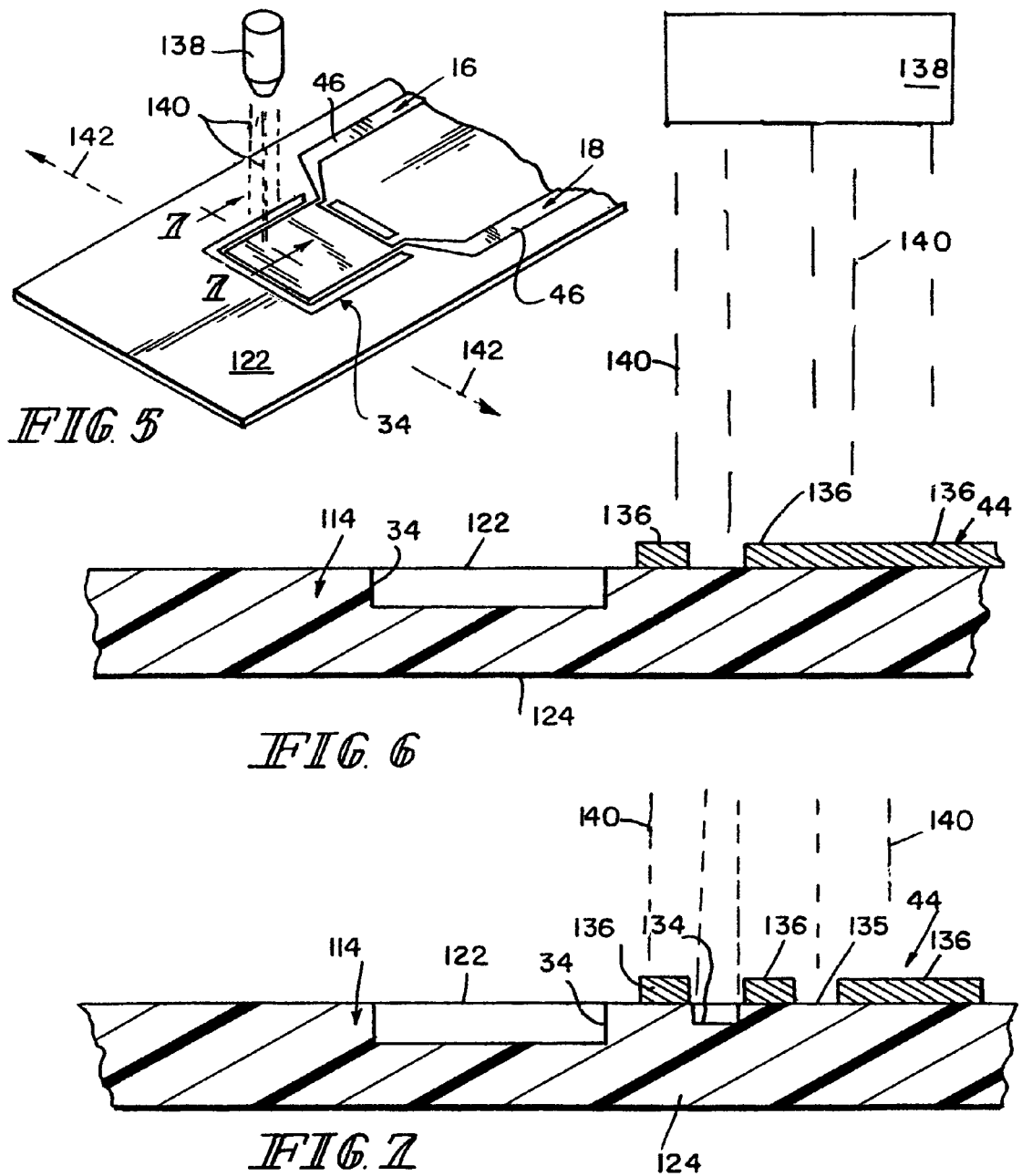

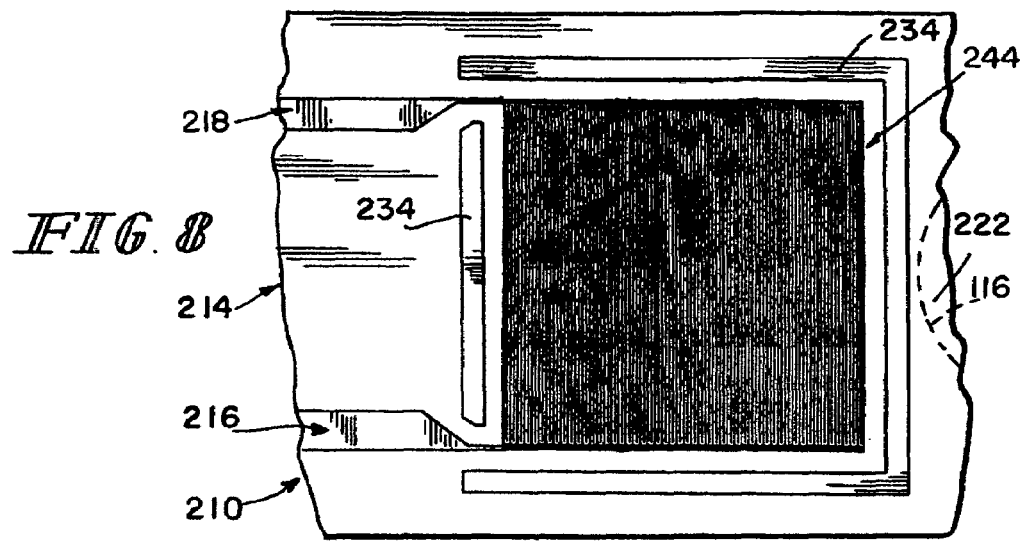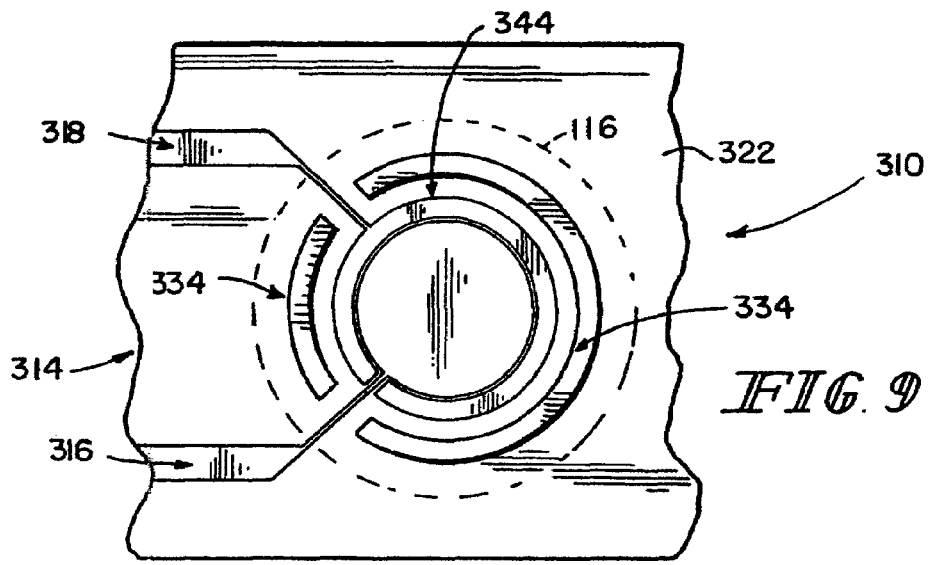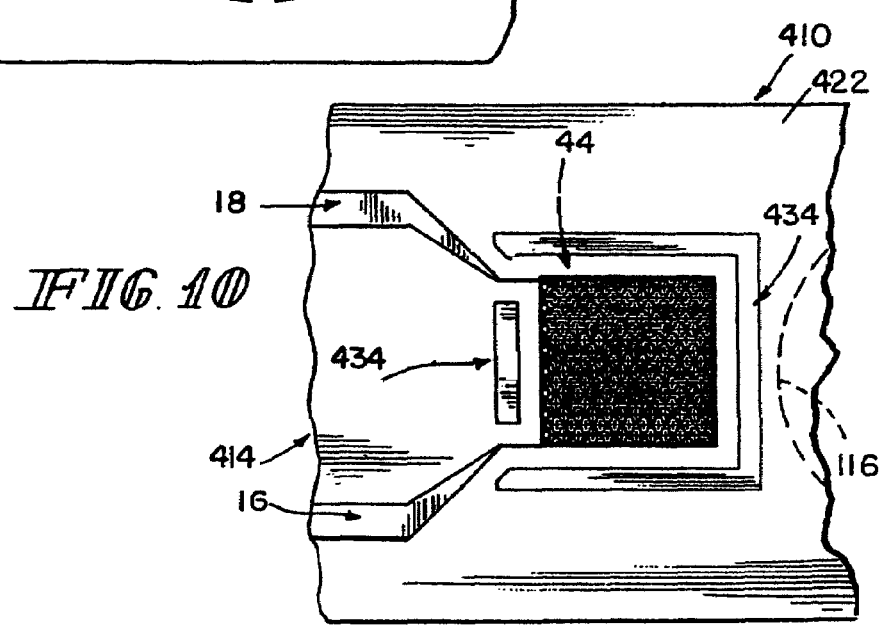

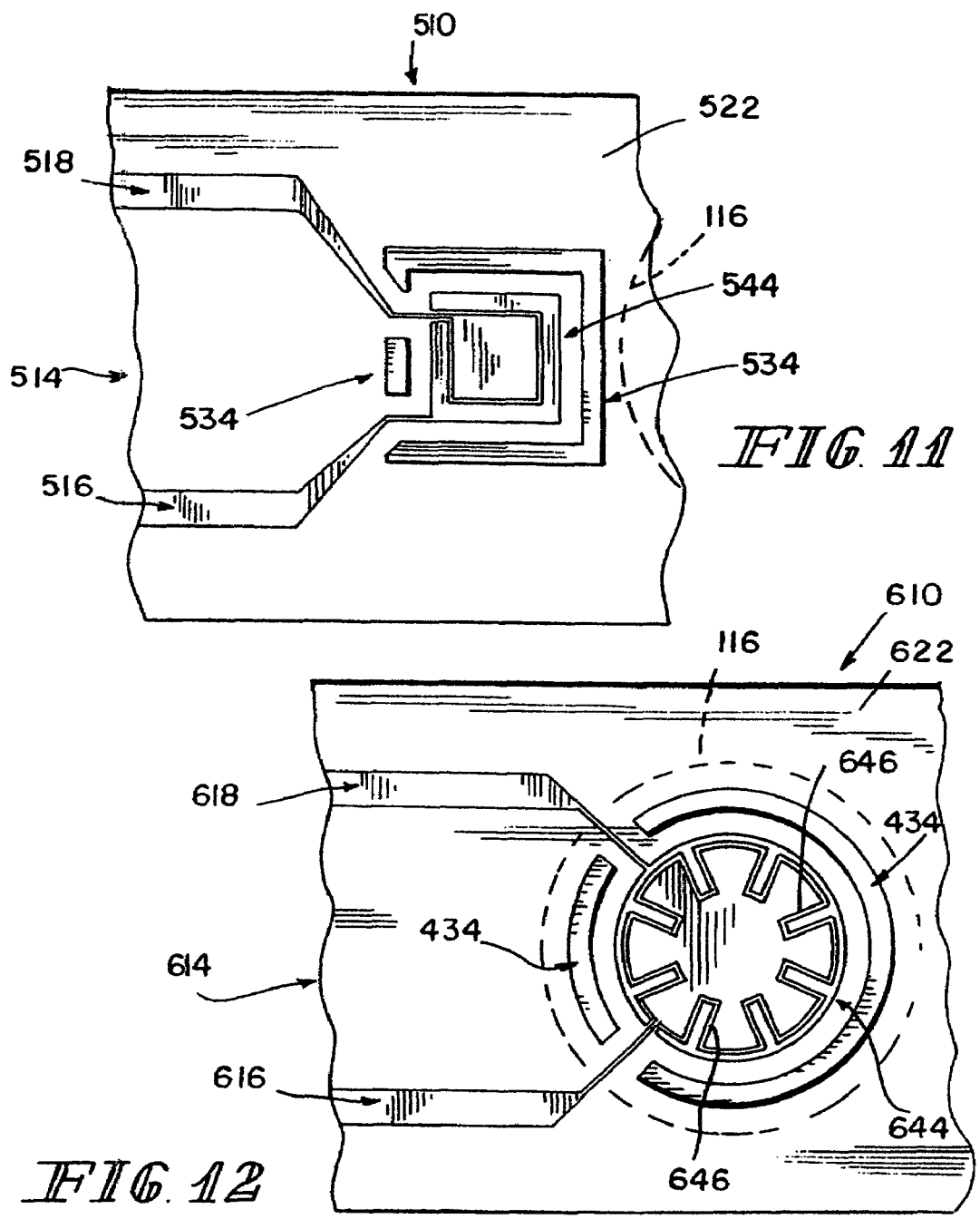

BIOSENSOR

FIELD OF THE INVENTION

The present invention relates to a biosensor and particularly to biosensor that includes at least one recess.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,413,690; 5,762,770; 5,798,031; and 5,997,817, the disclosure of each of which are hereby incorporated by reference. Laser ablation is a known technique the uses a laser to remove a material. See, for example, U.S. Pat. Nos. 5,576,073 and 5,593,739, the disclosure of each of which is expressly incorporated herein by reference. Such known laser ablation systems use a high power excimer laser, such as a krypton fluoride excimer laser with an illumination wavelength of 248 nanometers, to remove surface material. Die cutting processes have been also used to form reagent wells that include walls that hold or retain liquid reagents on the sensor strip in place while they dry. See, for example, U.S. Pat. Nos. 4,225,410 and 5,288,636.

According to the present invention a biosensor is provided. The biosensor comprises a plate element formed to include a pre-determined reaction zone and a recess positioned adjacent to the reaction zone. In addition, the biosensor comprises a reagent positioned on at least a portion of the reaction zone.

According to another aspect of the present invention, a biosensor is provided that comprises a bottom plate element including a first surface formed to include a recess therein, a reagent positioned on the first surface, and a top plate element coupled to the bottom plate element. In addition, the reagent covers at least a portion of the recess.

Still further, in accordance with the present invention, an electrode set is provided. The electrode set comprises a plate element formed to include a recess therein, electrodes positioned on the plate element and cooperating to define an electrode array, and a reagent positioned on at least a portion of the electrodes. In addition, the recess circumscribes at least a portion of the electrode array.

In accordance with yet another aspect of the present invention a method of forming a biosensor is provided. The method comprises the steps of providing a plate element, forming at least one recess in the plate element, and applying a reagent onto the plate element to define a reaction zone. In addition, at least one recess circumscribes at least a portion of the reaction zone.

Additional features of the invention will become apparent to those skilled in the art upon consideration of the following detailed description of the preferred embodiment exemplifying the best mode of carrying out the invention

BRIEF DESCRIPTION OF THE DRAWINGS

The detailed description particularly refers to the accompanying figures in which:

FIG. 5 is a perspective view of the bottom plate element and tracks of the biosensor of FIG. 3, showing a laser ablator forming grooves in the tracks;

FIG. 6 is an enlarged side view of the bottom plate element and tracks of FIG. 5;

FIG. 7 is a view taken along lines 7-7 of FIG. 5;

FIG. 8 is a plan view of an electrochemical biosensor in accordance with another aspect of the invention, showing the biosensor including a top plate element having an aperture (in phantom), a bottom plate element, an electrode array defining an electrochemical area, and recesses circumscribing at least a portion of the electrochemical area;

FIG. 9 is a plan view of an electrochemical biosensor in accordance with yet another aspect of the invention, showing the biosensor including a top plate element having an aperture (in phantom), a bottom plate element, a circular-shaped electrode array defining an electrochemical area, and recesses circumscribing at least a portion of the electrochemical area;

FIG. 10 is a plan view of an electrochemical biosensor in accordance with still another aspect of the invention, showing the biosensor including a top plate element having an aperture (in phantom), a bottom plate element, a rectangular-shaped electrode array defining an electrochemical area, and recesses circumscribing at least a portion of the electrochemical area;

FIG. 11 is a plan view of an electrochemical biosensor in accordance with another aspect of the invention, showing the biosensor including a top plate element having an aperture (in phantom), a bottom plate element, an electrode array defining an electrochemical area, and recesses circumscribing at least a portion of the electrochemical area;

FIG. 12 is a plan view of an electrochemical biosensor in accordance with another aspect of the invention, showing the biosensor including a top plate element having an aperture (in phantom), a bottom plate element, a wheel-shaped electrode array having spokes and defining an electrochemical area, and recesses circumscribing at least a portion of the electrochemical area;

DETAILED DESCRIPTION OF THE DRAWINGS

A biosensor 10 in accordance with the present invention provides a plate element with at least one recess formed therein. The recesses formed in the plate element may be discrete or one continuous recess may be formed in the plate element. Each recess can be formed in a variety of diagnostic biosensors including, for example, electrochemical and photometric biosensors. The purpose of the recess is to control fluid flow on the plate element and/or to provide a high-capillary edge to a liquid sample, for the sake of retaining the sample within a circumscribed boundary. Various aspects of the invention are presented in FIGS. 1-17, which are not drawn to scale and wherein like components in the several views are numbered alike.

Figure 1:
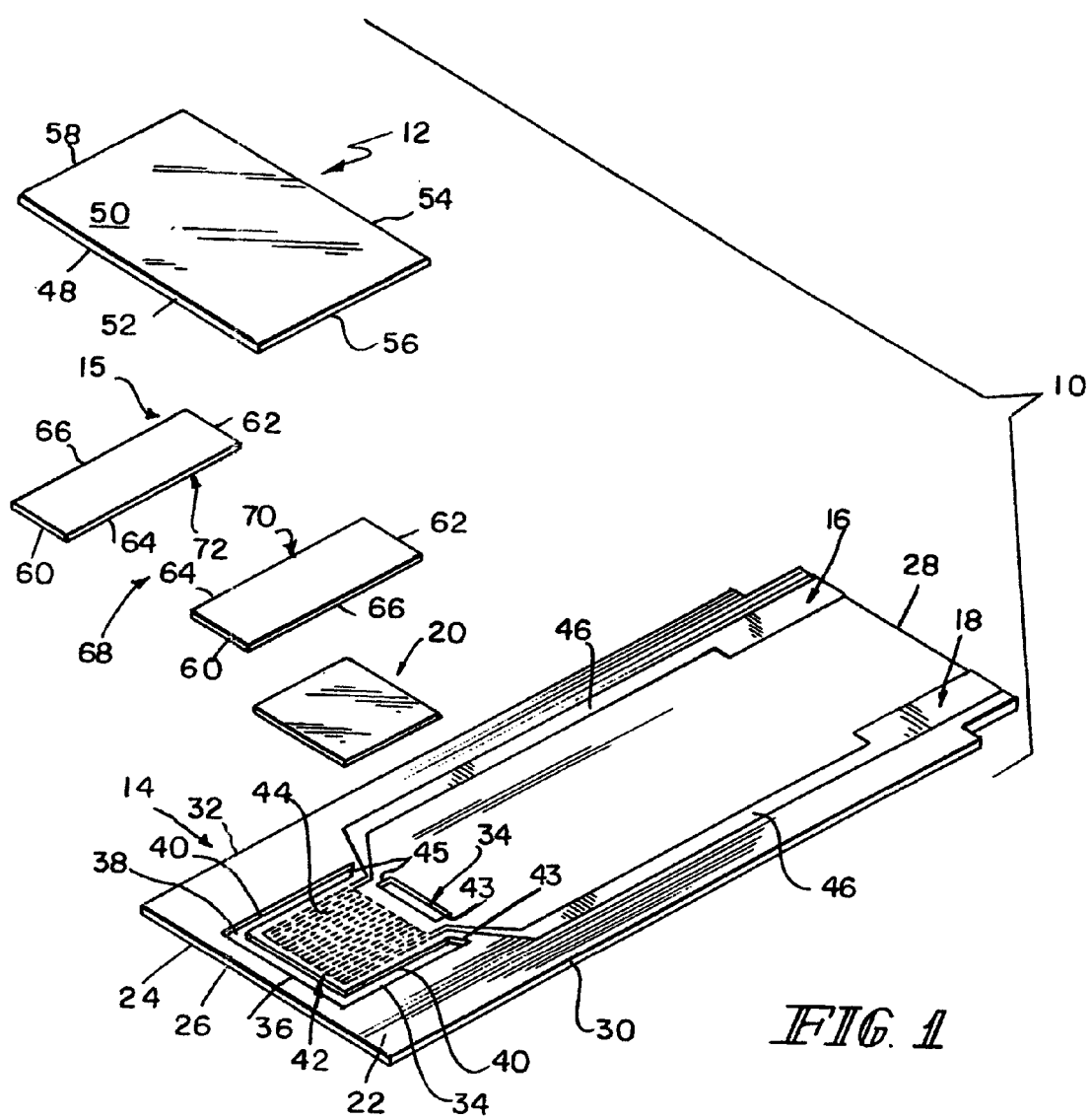
FIG. 1 is an exploded assembly view of an electrochemical biosensor in accordance with the present invention.
Figure 2:
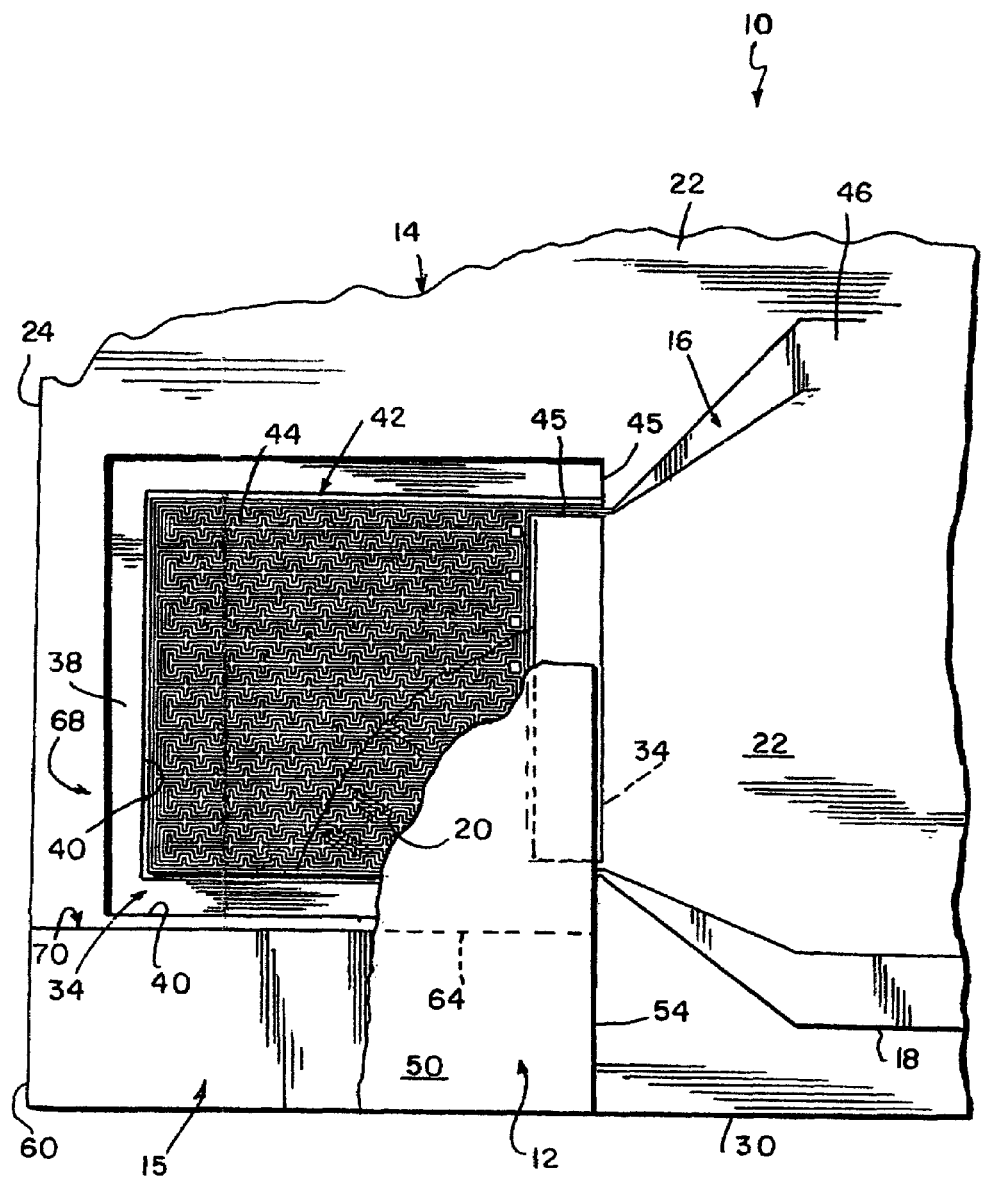
FIG. 2 is an enlarged view with portions broken away of the biosensor of FIG. 1.
Figure 3:
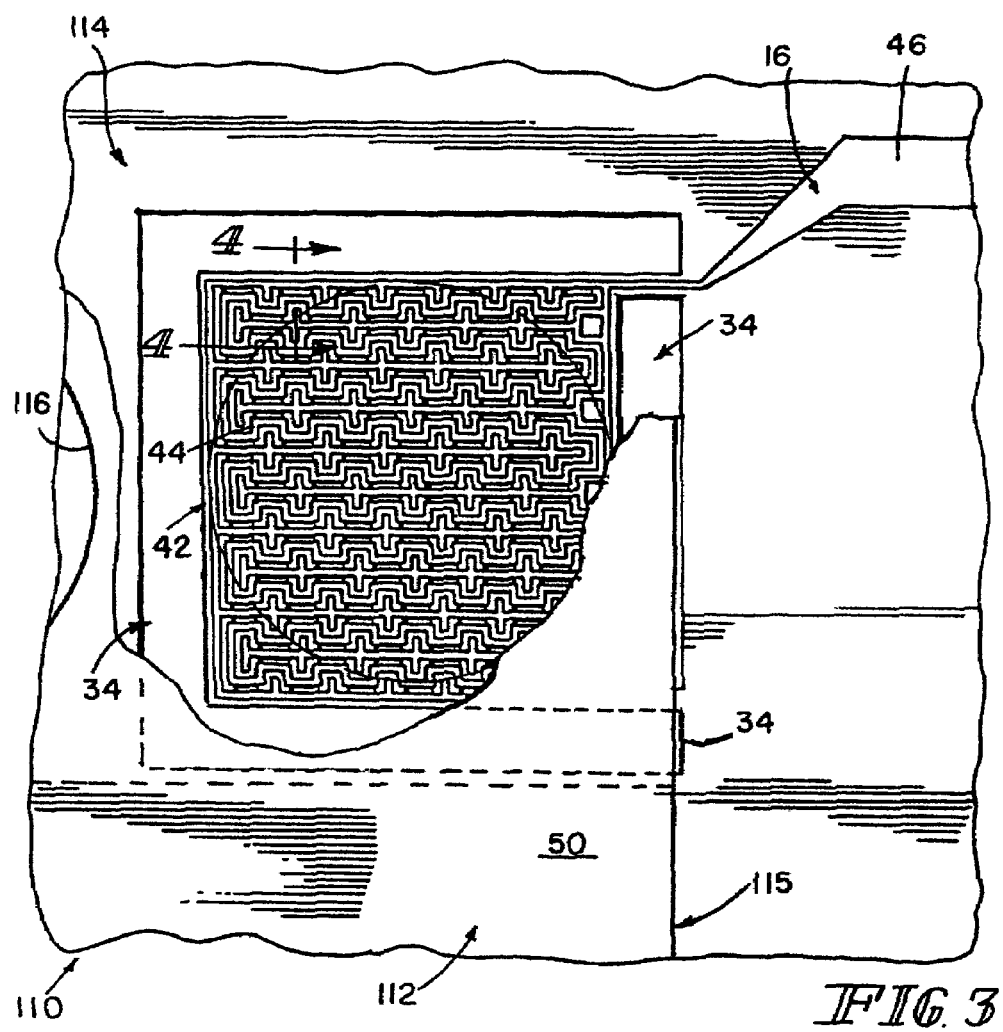
FIG. 3 is an enlarged view of an electrochemical biosensor in accordance with another aspect of the invention showing the biosensor including top and bottom plate elements and electrically conductive tracks.

FIGS. 1-2 illustrate an aspect of the invention in the form of an electrochemical biosensor 10 having a top plate element 12, a bottom plate element 14 formed to include recesses 34, a spacer 15, electrically conductive tracks 16, 18, a reagent 20 extending over a portion of tracks 16, 18, and recesses 34 formed in plate element 14. Biosensor 10 is preferably rectangular in shape. It is appreciated, however, that biosensor 10 can assume any number of shapes in accordance with this disclosure. Biosensor 10 is preferably produced from rolls of material. Thus, when produced from rolls, the selection of materials for the construction of biosensor 10 necessitates the use of materials that are sufficiently flexible for roll processing, but which are still rigid enough to give a useful stiffness to finished biosensor 10.

Bottom plate element 14 of biosensor 10 includes a first surface 22 that supports conductive tracks 16, 18 and an opposite second surface 24. See FIG. 1. In addition, plate element 14 has opposite ends 26, 28 and edges 30, 32 extending between ends 26, 28. Bottom element 14 may be constructed from a wide variety of insulative materials. Non-limiting examples of insulative materials that provide desirable structural properties include glass, ceramics, vinyl polymers, polyimides, polyesters, and styrenics. Preferably, bottom element 14 is a flexible polymer, such as a polyester or polyimide. A non-limiting example of a suitable material is 5 mil thick Kaladex® plastic, a polyester commercially available from E.I. DuPont de Nemours, Wilmington, Del.

Additionally, recesses 34 are formed in first surface 22 of bottom plate element 14. Recesses 34 are formed in the shape of channels, have opposite ends 43, 45 and are each defined by a lip 36, a floor 38, and opposite walls 40 extending between lip 36 and floor 38. See FIG. 1. Opposite walls 40 define opposite sides of recesses 34. Walls 40 are spaced-apart and define a width of recess 34 that is less than about 1000 µm. Preferably, the width of recess 34 is about 10 µm to 750 µm. It is appreciated, however, that walls 40 may be situated at a variety of angles relative to perpendicular to floor 38, causing the width of recesses to vary in accordance with this disclosure. In addition, the height of the recess walls 40 is about 1 µm to 1500 µm. Preferably, the walls 40 have a height of about 1 µm to 100 µm, and most preferably of about 4 µm to. about 20 µm.

Biosensors in accordance with the present invention are each formed to include a pre-defined reaction area where the sensing takes place. When the biosensor is electrochemical, as shown in FIGS. 1-14 and 16-17, the pre-defined area is an electrochemical area that is located on a portion of the electrodes. Referring now to FIGS. 1-2, biosensor 10 includes an electrochemical reaction area 42, which is defined as the area of electrodes 44 where reagent 20 is located. Recesses 34 of biosensor 10 circumscribe about 90% of area 42. It is appreciated, however, that recesses formed in biosensors of this invention may circumscribe greater or less than 90% of area 42. Specifically, recesses 34 circumscribe at least about 44% of area 42, more preferably at least 70% of area 42, and most preferably at least 90% of area 42.

As shown in FIG. 2, electrically conductive tracks 16, 18 are created or isolated on first surface 24 of bottom element 14. Tracks 16, 18 represent the electrodes of biosensor 10. As used herein, the phrase "electrode set" is a set of at least two electrodes, for example 2 to 200, or 3 to 20, electrodes. These electrodes may, for example, be a working electrode and an auxiliary electrode. Tracks 16, 18 cooperate to form an interdigitated electrode array 44 positioned within the periphery of recesses 34 and leads 46 that extend from array 44 and between recesses 34 toward end 28.

Tracks 16, 18 are constructed from electrically conductive materials. Nonlimiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. Most preferably, track 16 is a working electrode made of gold, and track 18 is an auxiliary electrode that is also made of gold and is substantially the same size as the working electrode.

Tracks 16, 18 are isolated from the rest of the electrically conductive surface by laser ablation. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks 16, 18 are preferably created by removing the electrically conductive material from an area extending around the electrodes. Therefore, tracks 16, 18 are isolated from the rest of the electrically-conductive material on substrate 14 by a gap having a width of about 5 µm to about 500 µm, preferably the gap has a width of about 100 µm to about 200 µm. Alternatively, it is appreciated that tracks 16, 18 may be created by laser ablation alone on bottom substrate 14. Further, tracks 16, 18 may be laminated, screen-printed, or formed by photolithography in accordance with this disclosure.

Multi-electrode arrangements are also possible in accordance with this disclosure. For example, it is contemplated that a biosensor may be formed that includes an additional electrically conductive track (not shown). In a three-electrode arrangement, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode in accordance with this disclosure. It is appreciated that the number of tracks, as well as the spacing between tracks in array 44 may vary in accordance with this disclosure and that a number of arrays may be formed as will be appreciated by one of skill in the art.

Reagent 20 provides electrochemical probes for specific analytes and is applied onto bottom plate element 14 such that reagent 20 covers array 44. A liquid reagent 20 is placed onto array 44. Reagent 20 then spreads across array 44 until it reaches recesses 34. It is believed that when the reagent reaches the edges of the recesses 34, the surface energy between array 44 and top plate element 12 decreases below the surface tension of reagent 20 to retain reagent 20 onto array 44. Additionally, reagent 20 is pulled along the edges of recesses 34, which aids in the spreading of reagent 20 within the boundary of array 44. It is believed that edges of recesses 34 both act like a block and helps spread the reagent around the perimeter of array 44. Therefore, when an adequate pre-determined amount of liquid reagent is placed on plate element 14, reagent 20 spreads over the surface until it encounters recesses 34 to form a reagent profile that has a generally uniform thickness of chemistry, which allows for an accurate analysis. When, however, an excess amount of liquid reagent 34 is applied to plate element 14, reagent 20 will spill into recesses.

Although recesses 34, tracks 16, 18, and reagent 20 are illustratively positioned on bottom plate element 14, it is appreciated that recesses, tracks, and the reagent may be positioned on top cover of biosensor in accordance with this disclosure.

ethylene oxide (mean molecular weight of 100-900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is expressly incorporated herein by reference.

Non-limiting examples of enzymes and mediators that may be used in measuring particular analytes in biosensor 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

The choice of specific reagent 20 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg poly- In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

Referring again to FIG. 1, spacer 15 of biosensor 10 includes first and second portions 70, 72. Each portion 70, 72 of spacer 15 includes ends 60, 62 and edges 64, 66 extending between ends 60, 62. In addition, edges 64 of portions 70, 72 cooperate to define a gap 68 in assembled biosensor 10. See FIG. 2. Ends 62 of portions 70, 72 are also formed to be positioned spaced-apart from array 44 when biosensor is assembled. Moreover, spacer 15 cooperates with top and bottom plate elements 12, 14 to expose array 44 to a liquid sample being applied to biosensor 10 in gap 68. Spacer 15 is a double-coated adhesive tape that is coupled to bottom plate element 14 and tracks 16, 18. A non-limiting example of such an adhesive is 3M High Performance Double Coated Tape 9500 PC, commercially available from Minnesota Mining and Manufacturing Company, St. Paul, Minn. It is appreciated that spacer 15 may be constructed of a variety of materials and may be coupled to top and bottom plate elements 12, 14 using a wide variety of commercially available adhesives. Additionally, when surface 22 of element 14 is exposed and not covered by electrical conductor, spacer 15 may be coupled to plate element 14 by welding (heat or ultrasonic) in accordance with this disclosure.

Top plate element 12 of biosensor 10 includes a first surface 48 facing spacer 15 and an opposite second surface 50. See FIG. 1. In addition, top plate element 12 has opposite ends 52, 54 and edges 56, 58 extending between ends 52, 54. Preferably, top plate element 12 is a flexible polymer, such as a polyester or polyimide. A nonlimiting example of a suitable material is 5 mil thick ST505 MYLARS® polyester film commercially available from E. I. DuPont de Nemours, Wilmington, Del. The adhesive coat of spacer 15 couples top plate element 12 to bottom plate element 14. It is appreciated that top plate element 12 can also be coupled to spacer using a wide variety of commercially available adhesives or with welding (heat or ultrasonic) in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in cassette magazine, or packed in a blister packaging.

Biosensor 10 is used in conjunction with the following:

1. a power source in electrical connection with the electrodes and capable of supplying an electrical potential difference between the electrodes sufficient to cause diffusion limited electro-oxidation of the reduced form of the mediator at the surface of the working electrode; and 2. a meter in electrical connection with the electrodes and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby expressly incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, human serum is assayed with this invention.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

To manufacture biosensor 10 a roll of metallized film is fed through guide rolls into an ablation/washing and drying station. A laser system capable of ablating bottom plate element 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in a predetermined pattern, to form a ribbon of isolated electrode sets. The metallized film is further ablated, after the isolated electrode sets are formed to create recesses 34 positioned adjacent the electrochemical area. The ribbon is then passed through more guide rolls, with a tension loop and through an optional inspection camera. The camera is used for quality control in order to check for defects.

Reagent 20 is compounded and applied in a liquid form to the center of the electrochemical area 42 at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to array 44 in a liquid or other form and dried or semi-dried onto the center of the electrochemical area 42 in accordance with this disclosure.

In addition, a roll or top plate element material is fed into an assembly station along with a roll of spacer material. Liners on either side of the spacer material are removed in that station and the top plate element is applied to one side of the spacer material to form a top plate element/spacer subassembly. The top plate element/spacer subassembly is slit into the appropriate width for a row of biosensors 10.

Next, a new release liner is added to the side of the spacer material opposite the cover and the subassembly is wound into a roll.

The ribbon of the reagent-coated bottom plate element is unwound and fed into a sensor assembly station along with the top plate element/spacer subassembly. The liner is removed from the spacer and the subassembly is placed on bottom plate element 14 to cover reagent 20. Next, the assembled material is cut to form individual biosensors 10, which are sorted and packed into vials, each closed with a stopper, to give packaged sensor strips.

Although ablating recesses 34 is described herein, it is appreciated that the method of forming recesses 34 in bottom plate element 14 is also not limited. For example, the recesses may be formed by etching (e.g., using photoligographic methods) or otherwise removing a portion of the surface of top plate element 12. The nearest electrode edge is approximately 10 μm to 500 μm from the recess, preferably 100 μm to 400 μm from the recess, most preferably 200 μm to 300 μm from the recess. Biosensors that are formed with recesses in accordance with this disclosure yield a reagent profile with generally uniform thickness of chemistry. A generally uniform thickness of chemistry allows for more accurate sample analysis.

The processes and products described above include a disposable biosensor, especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes.

Referring now to FIGS. 3-7, biosensor 110 is provided in accordance with this invention. Biosensor 110 includes a top plate element 112, a bottom plate element 114, and a spacer 115. Biosensor 110 is preferably rectangular in shape. It is appreciated, however, that biosensor 110 can assume any number of shapes in accordance with this disclosure. Biosensor 110 is preferably produced from rolls of material. Thus, the selection of materials for the construction of biosensor 110 necessitates the use of materials that are sufficiently flexible for roll processing, but which are still rigid enough to give a useful stiffness to finished biosensor 110.

Top plate element 112 of biosensor 110 is formed similarly to top plate element 12, except that element 112 is greater in length and is formed to include an aperture 116. See FIG. 3. Aperture 116 is spaced-apart from array 44 upon assembly of biosensor 110 can be positioned in a variety of locations, so long as the liquid sample flows from aperture 116 to array 44. In addition, bottom plate element 114 of biosensor 110 includes a first surface 122 that supports conductive tracks 16, 18 and an opposite second surface 124. See FIGS. 3-4.

Bottom element 114 may be constructed from a wide variety of insulative materials, similar to bottom element 14. Bottom plate element 114 includes a first surface 122 that supports conductive tracks 16, 18 and an opposite second surface 124. Tracks 16, 18 are created on surface 122 by removing substantially all of the electrically conductive material from the surface 122, except for a metallized electrode pattern 136 of array 44.

Multiple recesses 134 are formed in bottom plate element 114 within metallized electrode pattern 136 of array 44. In preferred embodiments, recesses 134 are formed by ablating first through the metallized film of array 44 (FIG. 6) to form gaps 135 of electrode pattern 136 and then through surface 122 of bottom plate element 114 (FIG. 7). Reagent 20 bleeds across array 44 and into recesses 134 positioned within pattern 136, forming a generally uniform thickness of chemistry across array 44. See FIG. 4. Reagent 20 will cover array 44 without extending into recesses 34, unless an excess amount or reagent 20 is applied to plate element 114. If excess reagent is applied to plate element 114, recesses 34 will retain the excess reagent.

Figure 4:
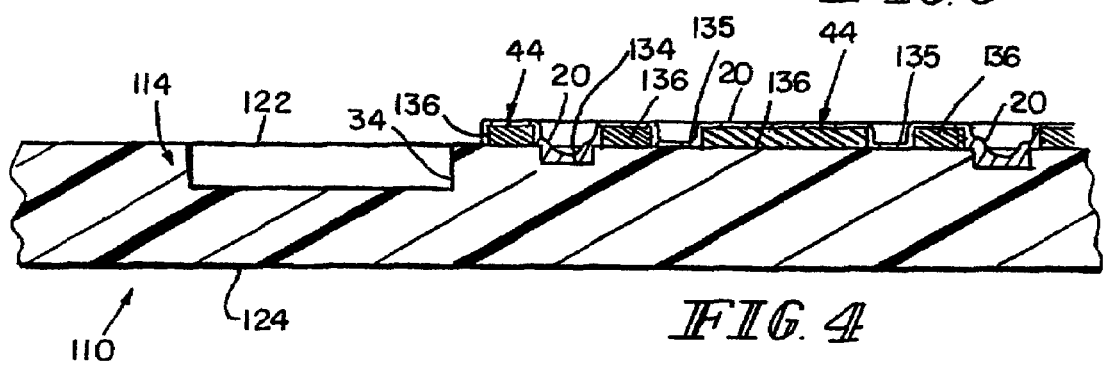
FIG. 4 is a view taken along lines 4-4 of FIG. 3.

Spacer 115 of biosensor 110 is formed similarly to spacer 15, except that spacer 115 is greater in length. See FIG. 3. Spacer 115 cooperates with plate elements 112, 114 to expose array 44 to a liquid sample being applied to biosensor 10. Although spacer 115 is illustratively formed of a double-sided adhesive tape, it is appreciated that spacer 115 cam be formed of a variety of materials and be coupled to bottom plate element 114 using a wide variety of commercially available adhesives or when portions of surface 22 are exposed, with welding (heat or ultrasonic) in accordance with this disclosure. To create recesses 134 within pattern 126, bottom plate element 114 moves relative to laser 138 along the x-y axis as shown by arrows 142 in FIG. 5. The patterned mask (not shown) may also move along the x-y axis so that array 44 is exposed to a second pulse of the laser light 140 (FIG. 7) to ablate surface 122 in a pattern conforming to the mask design. This subsequent pulsing ablates surface 122 to form multiple recesses 134 as shown in FIGS. 4 and 7. It is appreciated that the number and depths of recesses 134 formed in array may vary depending upon the reagent selected in accordance with this disclosure. Once array 44 and recesses 34, 134 are formed in plate element 114, biosensor 110 is assembled in a manner similar to biosensor 10 as described above. It is appreciated, however, that tracks 16, 18 may also be formed as discussed above with reference to biosensor 10.

It is appreciated that a variety of biosensors can be manufactured in accordance with this disclosure that have a variety of recess and electrode patterns, non-limiting examples of which are shown in FIGS. 8-16. Referring now to FIG. 8, a biosensor 210 is provided in accordance with the present invention. Biosensor 210 includes top plate element 112 formed to include aperture 116 and a vent (not shown) spaced-apart from aperture 116. Biosensor 210 also includes a bottom plate element 214 that supports electrically conductive tracks 216, 218. Tracks 216, 218 cooperate to form an interdigitated electrode array 244 positioned within the periphery of recesses 234. Except for the specific patterning, tracks 216, 218 are formed of similar materials and in a similar manner as tracks 16, 18. Recesses 234 are formed in a first surface 222 of bottom plate element 214. Biosensor 210 includes two recesses, one of which is generally linear in shape and one of which has three legs that extend about three sides of array 244. The recesses cooperate with one another to form a generally rectangular shape that extends about array 244. Except for the specific patterning of recesses 234, biosensor 210 is manufactured in a manner similar to biosensor 10 as described above.

As shown in FIG. 9, a biosensor 310 is provided in accordance with the present invention. Biosensor 310 includes top plate element 112 formed to include recess 116 and a bottom plate element 314. Bottom plate element 314 supports electrically conductive tracks 316, 318 that cooperate to form an interdigitated electrode array 344 positioned within the periphery of recesses 334 that are formed in element 314. Except for the specific patterning, tracks 316, 318 are formed of similar materials and in a similar manner as tracks 16, 18. Electrode array 344 is generally circular in shape and in general alignment with aperture 116. A detergent-impregnated mesh is preferably positioned between array 344 and top plate element 112. This mesh is preferably a polyester monofilament mesh from Sefar America, Inc. Briarcliff Manor, N.Y. It is appreciated that biosensor 310 may be constructed using a variety of commercially available meshes or may even be constructed without mesh in accordance with this disclosure.

In addition, recesses 334 are formed in a first surface 322 of bottom plate element 314. Biosensor 310 includes two recesses, one of which is general C-shaped and one of which is generally curved that cooperates with the first recess to form a generally circular shape. It is appreciated that the degree of curvature of recesses 334 may vary depending upon the size of array 344 and the positioning of tracks 316, 318 on bottom plate element 314. Except for the specific patterning of recesses 334 and array 344 and the application of the mesh (not shown) over array 344, biosensor 310 is manufactured in a manner similar to biosensor 10 as described above. It is appreciated a variety of methods may be used to apposition the mesh upon the electrode array 344.

FIG. 10 illustrates a biosensor 410 in accordance with the present invention. Biosensor 410 includes top plate element 112 formed to include aperture 116 and a bottom plate element 414. Bottom plate element 414 supports electrically conductive tracks 16, 18 as described above with reference to biosensor 10. Bottom plate element 414 has recesses 434 formed in a first surface 422. Biosensor 410 includes two recesses, one of which is generally linear in shape and one of which has three legs that extend about three sides of the rectangular-shaped array 44. Two end legs of the second recess 234 include tapered ends. Recesses 434 cooperate with one another to form a generally rectangular shape. In addition, recesses 434 are spaced-apart from array 44 on first surface 422 of bottom plate element 414. Except of the specific patterning of recesses 434, biosensor 410 is manufactured in a manner similar to biosensor 110 as described above.

FIG. 11 illustrates a biosensor 510 in accordance with the present invention. Biosensor 510 includes top plate element 112 formed to include aperture 116 and a bottom plate element 514. Bottom plate element 514 supports electrically conductive tracks 516, 518 that cooperate with one another to form an electrode array 544. Except for the specific patterning, tracks 516, 518 are formed of similar materials and in a similar manner as tracks 16, 18. Biosensor 510 also includes recesses 534 formed in a first surface 522 of bottom plate element 514. Biosensor 510 includes two recesses, which are formed similarly to recesses 434, except for their relative lengths. Recesses 534 are also spaced-apart from array 544 on first surface 522 of bottom plate element 514. Except of the specific patterning of recesses 534 and array 544, biosensor 510 is manufactured in a manner similar to biosensor 110 as described above.

FIG. 12 illustrates a biosensor 610 in accordance with the present invention. Biosensor 610 includes top plate element 112 formed to include aperture 116 and a bottom plate element 614. Bottom plate element 614 supports electrically conductive tracks 616, 618 that cooperate with one another to form an electrode array 644. Except for the specific patterning, tracks 616, 618 are formed of similar materials and in a similar manner as tracks 16, 18. Electrode array 644 is shaped similarly to a wheel and includes eight spokes 646 that extend toward the center of the wheel. In addition, array 644 is positioned to lie in general alignment with aperture 116. Mesh, as described above with reference to biosensor 310, is preferably positioned between array 644 and top plate element 112. It is appreciated that a wide variety of commercially available mesh may be used in accordance with this disclosure.

In addition, recesses 434 are formed in a first surface 622 of bottom plate element 614. It is appreciated that the degree of curvature of recesses 434 may vary depending upon the size of array 644 and the positioning of tracks 616, 618 on bottom plate element 614. Except of the patterning of recesses 434 and array 644, biosensor 610 is manufactured in a manner similar to biosensor 110 as described above.

Figure 13:
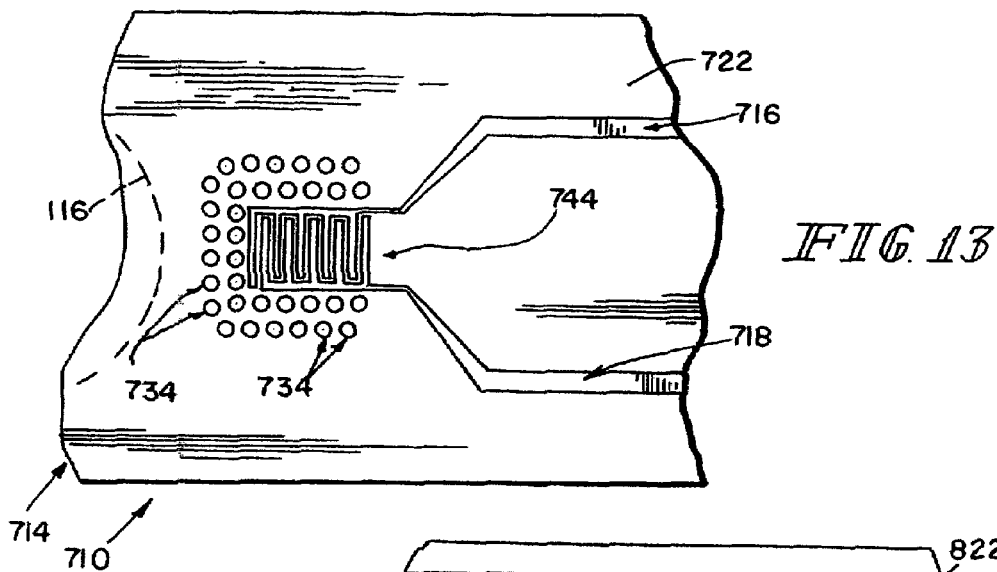
FIG. 13 is a plan view of an electrochemical biosensor in accordance with another aspect of the invention, showing the biosensor including a top plate element having an aperture (in phantom), a bottom plate element, an interdigitated electrode array defining an electrochemical area, and a plurality of discrete circular-shaped recesses spaced-apart from one another and circumscribing at least a portion of the electrochemical area.

A biosensor 710 in accordance with the present invention is illustrated in FIG. 13. Biosensor 710 includes top plate element 112 formed to include aperture 116 and a bottom plate element 714. Bottom plate element 714 supports electrically conductive tracks 716, 718 that cooperate with one another to form an electrode array 744. Except for the specific patterning, tracks 716, 718 are formed of similar materials and in a similar manner as tracks 16, 18. In addition, recesses 734 are formed in a first surface 722 of bottom plate element 714. Illustratively, biosensor 710 includes thirty-four recesses 734 that are formed as spaced-apart circular-shaped apertures in first surface 722. It is appreciated that biosensor 710 may include greater or fewer than thirty-four recesses in accordance with this disclosure. Further, it is appreciated that recesses 734 may be formed in a variety of shapes and sizes in accordance with this disclosure. Except of the patterning of recesses 734 and array 744, biosensor 710 is manufactured in a manner similar to biosensor 110 as described above.

Figure 14:
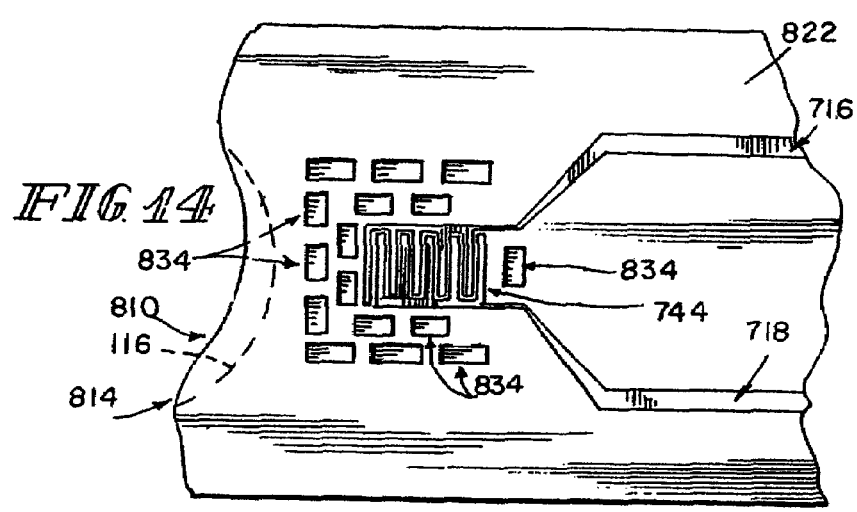
FIG. 14 is a plan view of an electrochemical biosensor in accordance with another aspect of the invention, showing the biosensor including a top plate element having an aperture (in phantom), a bottom plate element, an interdigitated electrode array defining an electrochemical area, and a plurality of discrete rectangular-shaped recesses spaced-apart from one another and circumscribing at least a portion of the electrochemical area.

A biosensor 810 in accordance with the present invention is shown in FIG. 14. Biosensor 810 includes top plate element 112 formed to include aperture 116 and a bottom plate element 814. Bottom plate element 814 supports electrically conductive tracks 716, 718 that cooperate with one another to form electrode array 744. In addition, recesses 834 are formed in a first surface 822 of bottom plate element 814. Illustratively, biosensor 810 includes sixteen recesses 834 that are formed as spaced-apart rectangular-shaped apertures in first surface 822. It is appreciated that biosensor 810 may include greater or fewer than sixteen recesses 834 and may be formed in a variety of shapes and sizes in accordance with this disclosure. Biosensor 810 is manufactured in a manner similar to biosensor 110 as described above, except of the patterning of recesses 834 and array 744.

Figure 15:
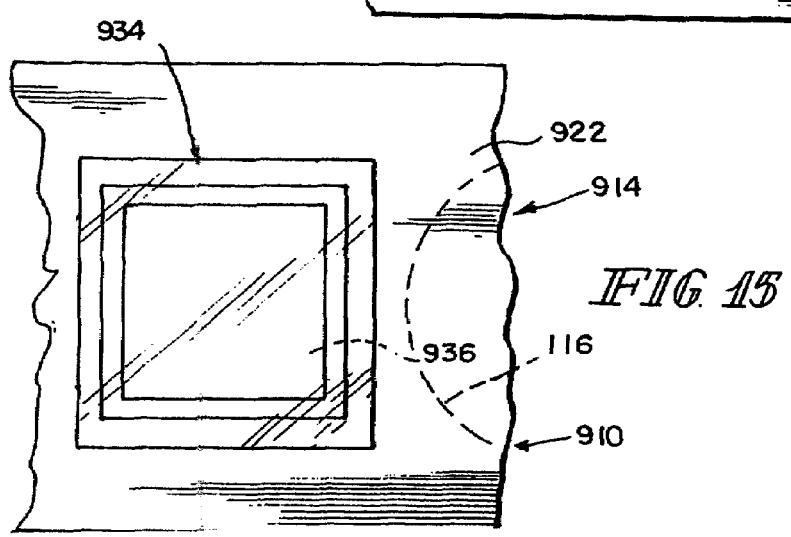
FIG. 15 is a plan view of a photometric biosensor in accordance with another aspect of the invention, showing the biosensor including a top plate element having an aperture (in phantom), a bottom plate element having a pre-defined reaction zone, a continuous recess circumscribing the reaction zone, and a reagent positioned within the zone and extending into the recess.

Referring now to FIG. 15, a biosensor 910 is formed in accordance with the present invention. Biosensor 910 includes top plate element 112 formed to include aperture 116 and a bottom plate element 914. Bottom plate element 914 includes a continuous recess 934 extending about a pre-defined reaction zone 936, where a reagent is located and sensing takes place on biosensor 910. Illustratively, biosensor 910 is formed to make a photometric measurement of an analyte in a biological fluid.

The following non-limiting example is given for the purpose of illustrating a reagent suitable for use with biosensor 910 that is formed to test cholesterol.

0.117 g methyl hydroxpropylcellulose (Culminal MHPC 8800)

7.000 g. titanium dioxide 0.138 g monopotassium dihydrogen phosphate 0.479 g disodium monohydrogen phosphate hydrate 3400 U cholesterol esterase 5000 U cholesterol oxidase $7 \times 10^4$ U peroxidase 0.476 g. sodium dioctyl sulphosuccinate are dissolved in 70 ml. water. There are then successively homogeneously incorporated 14.0 g. cellulose 8.4 g. polyvinyl propionate dispersion.

Finally, there is Added:

0.66 g. 3,3',5,5'-tetramethylbenzidine, dissolved in 1.6 ml. acetone. This batch is coated in approximately 300 µ thick layer onto bottom plate element 914. See U.S. Pat. No. B1 4,477,575, to Vogel et al. the disclosure of which is expressly incorporated herein by reference. It is appreciated, that any number of photometric reagents may be used with biosensor 910 in accordance with the present invention.

To manufacture biosensor 910, top plate element 912 is formed in a manner similar to top plate element 112. To form bottom plate element 914 a roll of nonmetallized film is fed through guide rolls into an ablation/washing and drying station as described above. In the laser ablator, the film is ablated in a pre-determined recess pattern 934 that is formed to extend about reaction zone 936. The resulting ablated material is then passed through more guide rolls, with a tension loop and through an optional inspection camera. The camera is used for quality control in order to check for defects.

The reagent is compounded and applied in a liquid form to the center of reaction zone 936 at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to area 42 in a liquid or other form and dried or semi-dried onto the center of the electrochemical area 42 in accordance with this disclosure.

In addition, a roll or top plate element material is fed into an assembly station along with a roll of spacer material. Liners on either side of the spacer material are removed in that station and the top plate element is applied to one side of the spacer material to form a top plate element/spacer subassembly. The top plate element/spacer subassembly is slit into the appropriate width for a row of biosensors 910. Next, a new release liner is added to the side of the spacer material opposite the cover and the subassembly is wound into a roll.

The ribbon of the reagent-coated bottom plate element is unwound and fed into a sensor assembly station along with the top plate element/spacer subassembly. The liner is removed from the spacer and the subassembly is placed on bottom plate element 914 to cover the reagent. Next, the assembled material is cut to form individual biosensors 910, which are sorted and packed into vials, each closed with a stopper, to give packaged sensor strips.

Figure 16:
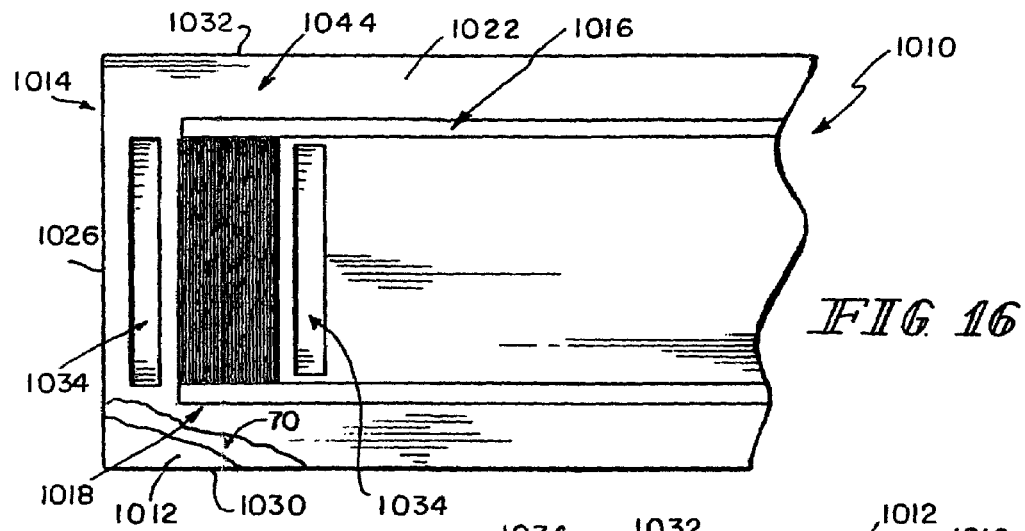
FIG. 16 is a plan view with portions broken away of an electrochemical biosensor in accordance with another aspect of the invention.
Figure 17:
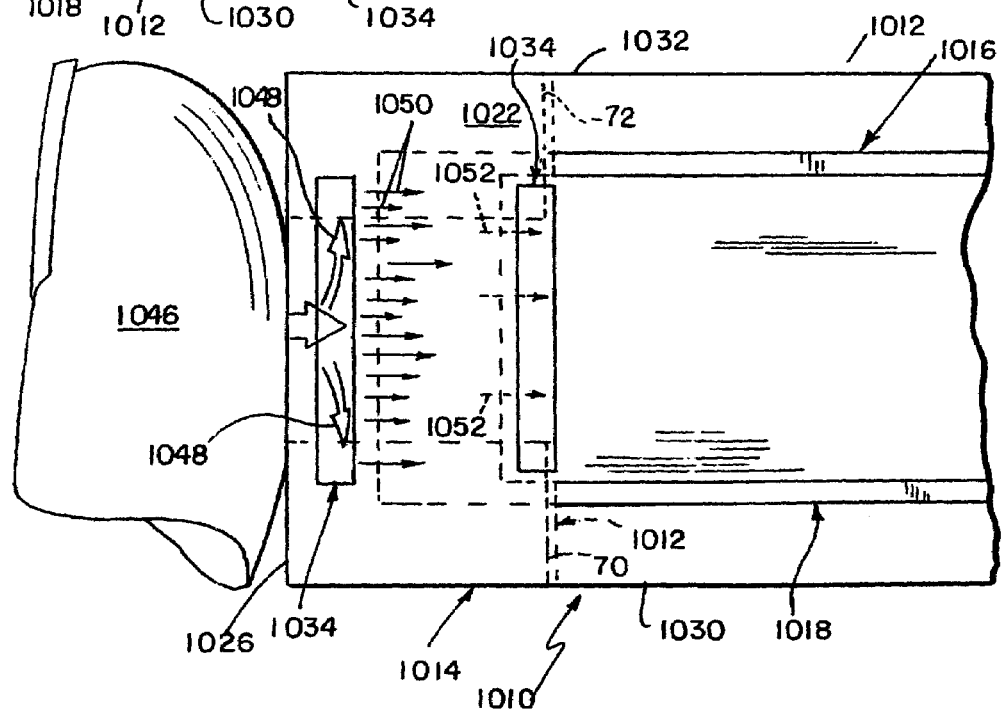
FIG. 17 is a view similar to FIG. 16, showing a liquid sample being applied to the biosensor.

As shown in FIGS. 16-17, a biosensor 1010 is provided in accordance with the present invention. Biosensor 1010 controls the fluid flow of the reagent during assembly as well as the fluid flow of a liquid sample being applied to biosensor 1010. Biosensor 1010 has a top plate element 1012, a bottom plate element 1014, and first and second portions 70, 72 of spacer 15 positioned to lie between top and bottom plate elements 1012, 1014.

Bottom plate element 1014 of biosensor 1010 includes a first surface 1022 that supports conductive tracks 1016, 1018. See FIG. 16. Except for the specific patterning, tracks 1016, 1018 are formed of similar materials and in a similar manner as tracks 16, 18. In addition, plate element 1014 has an end 1026 and edges 1030, 1032 extending from end 1026. Bottom element 1014 may be constructed from a wide variety of insulative materials similar to bottom element 14. Additionally, bottom plate element 1014 is formed to include recesses 1034 in first surface 1022. Illustratively, biosensor 1010 includes two spaced-apart linear-shaped recesses that lie on either side of array 1044. It is appreciated that recesses 1034 may be formed in a variety of shapes and sizes in accordance with this disclosure. Recess 1034 adjacent to end 1026 is formed to distribute a liquid sample in a direction generally parallel to end 1026 before the liquid sample engages array 1044. Biosensor 1010 is constructed in a manner similar to biosensor 10.

In use, a user of biosensor 1010 places a finger 1046 adjacent to end 1026. A liquid sample flows in direction of arrows 1048 into first recess 1034 as shown in FIG. 17. Once sample has filled recess 1034, sample flows in direction of arrow 1050 across electrode array 1044, where the sensing of biosensor 1010 takes place. Sample, eventually passes over array 1044 and flows into second recess 1034 as shown by arrows 1052. Second recess acts as a reservoir for liquid sample for purposes of distributing the sample across array 1044. Recesses 1034 of biosensor 1010 cooperate with one another to enable the manufacturer to achieve a reagent profile with generally uniform thickness of chemistry. In addition, recesses 1034 spreads liquid sample on bottom plate element 1014 in a direction generally perpendicular to fluid flow (see arrows 1048) so that the contact area of electrode array 1044 is maximized. The top and bottom plate elements 1012, 1014 are assembled as discussed above with reference to biosensor 110.

Although the invention has been described in detail with reference to a preferred embodiment, variations and modifications exist within the scope and spirit of the invention as described and defined in the following claims.

What is claimed is:

1. A method of forming an electrode set, comprising:
   providing a plate element
   forming recesses in the plate element;
   positioning electrodes on the plate element, the electrodes cooperating to define an interdigitated electrode array, and
   positioning a reagent on at least a portion of the electrodes, wherein at least one recess circumscribes at least a portion of the electrode array and wherein at least one recess is positioned within the electrode array.

2. The method of claim 1, wherein at least one of the recesses has a width that is less than 1000 µm.

3. The method of claim 1, wherein at least one recess has a width of 1 µm to 250 µm.

4. A method of forming a biosensor, the method comprising:
   providing a top plate element and a bottom plate element, the bottom plate element having a first surface and a pre-determined reaction zone on the first surface,
   forming a recess in the first surface adjacent to and circumscribing at least a portion of the reaction zone;
   coating a reagent on at least a portion of the reaction zone; and extending the top plate element across the reagent so that the top plate element cooperates with the bottom plate element to define a gap, the gap having a sample opening and being sized to transport a liquid sample from the opening to the reagent, wherein at least a portion of the recess is positioned in the gap between the sample opening and the reagent.

5. The method of claim 4, wherein the recesses are formed by laser ablation.

6. The method of claim 5, wherein the recesses are formed by laser ablation.

7. The method of claim 4, wherein discrete recesses are formed in the plate element.

8. The method of claim 7, further comprising the step of forming electrodes on the reaction zone and the reagent engages at least a portion of the electrodes.

9. The method of claim 8, wherein at least one of the recesses is formed to be linear in shape.

10. The method of claim 8, wherein the recesses cooperate with one another to circumscribe at least a portion of the reaction zone.

11. The method of claim 7, wherein at least one recess is formed to have a width that is less than 1000 μm.

12. The method of claim 7, wherein at least one recess is formed to have a width of 1 μm to 250 μm.

13. The method of claim 7, wherein the electrodes cooperate to define an electrode array with a pre-determined pattern.

14. The method of claim 7, wherein at least one of the recesses is fanned to be curved in shape.

15. The method of claim 14, wherein the recesses cooperate with one another to circumscribe at least a portion of the reaction zone.

16. The method of claim 4, wherein the recess is formed to have a width that is less than 1000 μm.

17. The method of claim 4, wherein the recess is formed to have a width of 1 μm to 250 μm.

18. The method of claim 4, wherein the recess has is formed to have height of 0.5 μm to 500 μm.

19. The method of claim 18, wherein the at least one wall is formed to have a height of 8 μm to 25 μm.

20. The method of claim 4, wherein the recess is formed to be rectangular in shape.

21. A method of Coming a biosensor, the method comprising:
providing a top plate element and a bottom plate element, the bottom plate element including a first surface;
forming a recess in the first surface;
positioning a reagent on the first surface adjacent to the recess; and
coupling the a top plate element to the bottom plate element so that the top plate element extends across the reagent and cooperates with the bottom plate element to define a gap, the gap having a sample opening and sized to transport a liquid sample from the opening to the reagent, wherein at least a portion of the recess is positioned in the gap between the sample opening and the reagent and the recess circumscribes at least a portion of the reagent.

22. The method of claim 21, further comprising the step of forming an electrode array having a pre-determined electrode pattern positioned between the top and bottom plate elements, wherein the reagent engages at least a portion of the electrode array.

23. The method of claim 22, wherein the biosensor includes two spaced-apart recesses.

24. The method of claim 23, wherein the recesses circumscribe at least a portion of the electrode array.

25. The method of claim 23, wherein the recesses are positioned within the electrode pattern of the array.

26. A method of forming a biosensor, the method comprises the steps of:
providing a plate element;
ablating at least one recess in. the plate element;
applying a reagent onto the plate element to define a reaction zone, wherein the at least one recess circumscribes at least a portion of the reaction zone; and
positioning a top plate element over the bottom plate element so that the top plate element extends across the reagent cooperates with the bottom plate element to create a gap having a liquid sample opening and at least a portion of at least one recess is positioned in the gap between the sample opening and the reaction zone.

27. The method of claim 26, further comprising the step of forming an electrode set in the reaction zone.

28. The method of claim 26, wherein the recesses are formed by laser ablation.

29. A method of forming a biosensor, the method comprising:
providing a plate element formed to include a first surface and a pre-determined reaction zone on the first surface,
forming discrete recesses in the first surface adjacent to and circumscribing at least a portion of the reaction zone;
positioning a reagent on at least a portion of the reaction zone; and
positioning electrodes on the reaction zone such that the electrodes cooperate to define an electrode array with a pre-determined pattern, wherein the reagent engages at least a portion of the electrodes and the discrete recesses are positioned within the pattern.

* * * * *

UNITED STATES PATENT AND TRADEMARK OFFICE
CERTIFICATE OF CORRECTION

PATENT NO. : 7,287,318 B2　　　　　　　　　　　　　　　　　　　　　　Page 1 of 1
APPLICATION NO. : 10/703408
DATED : October 30, 2007
INVENTOR(S) : Bhullar et al.

It is certified that error appears in the above-identified patent and that said Letters Patent is hereby corrected as shown below:

On the cover page, add --Related U.S. Application Data
(63) Continuation of application No. 09/684,257, filed on Oct. 6, 2000, now Pat. No. 6,645,359.--

Col. 1, line 1, add --CROSS-REFERENCE TO RELATED APPLICATION
This application is a continuation of U.S. Patent Application No. 09/684,257, filed October 6, 2000, now U.S. Pat. No. 6,645,359.--

Signed and Sealed this

Twenty-fourth Day of November, 2009

David J. Kappos
*Director of the United States Patent and Trademark Office*